(12) United States Patent
Abe

(10) Patent No.: US 8,790,630 B2
(45) Date of Patent: *Jul. 29, 2014

(54) PURE CHLORINE DIOXIDE SOLUTION, AND GEL-LIKE COMPOSITION AND FOAMING COMPOSITION EACH COMPRISING THE SAME

(75) Inventor: Koji Abe, Nishinomiya (JP)

(73) Assignee: Taiko Pharmaceutical Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/618,585

(22) Filed: Sep. 14, 2012

(65) Prior Publication Data

US 2013/0017165 A1    Jan. 17, 2013

Related U.S. Application Data

(62) Division of application No. 12/531,244, filed as application No. PCT/JP2008/052495 on Feb. 15, 2008.

(30) Foreign Application Priority Data

Mar. 15, 2007  (JP) ................................ 2007-067178

(51) Int. Cl.
*A61L 9/00* (2006.01)
*A61K 33/14* (2006.01)
*A61K 8/18* (2006.01)

(52) U.S. Cl.
USPC ........................... 424/76.21; 424/661; 424/65

(58) Field of Classification Search
CPC ....... A61K 33/00; A61K 33/14; A61K 33/40; C12N 9/18; A01N 59/00; C01B 11/024; C01B 11/022; C02F 1/50; C02F 2303/04
USPC ........................................ 424/65, 661, 76.21
See application file for complete search history.

(56) References Cited

U.S. PATENT DOCUMENTS

| 4,044,103 | A | | 8/1977 | Molland et al. |
| 4,104,190 | A | | 8/1978 | Hartshorn |
| 4,731,193 | A | * | 3/1988 | Mason et al. ................. 510/370 |
| 4,880,556 | A | | 11/1989 | Hutchings |
| 5,165,910 | A | | 11/1992 | Oikawa et al. |

(Continued)

FOREIGN PATENT DOCUMENTS

| JP | 36-8135 B1 | 6/1961 |
| JP | 49-111898 A | 10/1974 |

(Continued)

OTHER PUBLICATIONS

International Search Report dated May 1, 2008 in corresponding International Application No. PCT/JP2008/052495.

(Continued)

*Primary Examiner* — Blessing M Fubara
(74) *Attorney, Agent, or Firm* — Buchanan Ingersoll & Rooney PC

(57) ABSTRACT

A pure chlorine dioxide solution includes a chlorine dioxide gas dissolved therein, a chlorite, and a pH adjuster which is an acid or a salt thereof having a buffering property whose pH is 2.5 to 6.8 as a 5% aqueous solution at 25° C.

5 Claims, 1 Drawing Sheet

(56) References Cited

U.S. PATENT DOCUMENTS

| | | |
|---|---|---|
| 6,200,557 B1 | 3/2001 | Ratcliff |
| 6,238,643 B1 * | 5/2001 | Thangaraj et al. ............ 423/477 |
| 6,306,281 B1 * | 10/2001 | Kelley ......................... 205/556 |
| 2003/0113658 A1 | 6/2003 | Ebata et al. |
| 2005/0184273 A1 | 8/2005 | Morelli et al. |
| 2007/0202095 A1 | 8/2007 | Speronello et al. |

FOREIGN PATENT DOCUMENTS

| | | |
|---|---|---|
| JP | 61-19561 B2 | 5/1986 |
| JP | 61-181532 A | 8/1986 |
| JP | 63-309599 A | 12/1988 |
| JP | 1-319408 A | 12/1989 |
| JP | 4-46003 A * | 2/1992 |
| JP | 11-278808 A * | 10/1999 |
| JP | 3110724 B2 | 9/2000 |
| JP | 2007-217239 A | 8/2007 |

OTHER PUBLICATIONS

Kagaku Binran Kisohen, Sep. 25, 1966, p. 1054, Maruzen Co., Ltd. (cited in International Search Report).

* cited by examiner

PURE CHLORINE DIOXIDE SOLUTION, AND GEL-LIKE COMPOSITION AND FOAMING COMPOSITION EACH COMPRISING THE SAME

CROSS-REFERENCE TO RELATED APPLICATIONS

This application is a divisional of application Ser. No. 12/531,244, filed Sep. 14, 2009, which is the National Stage filing under §371 of PCT/JP2008/052495, filed Feb. 15, 2008, which in turn claims priority to Japanese Application No. 2007-067178, filed Mar. 15, 2007. the entire content of each of which is incorporated herein by reference.

TECHNICAL FIELD

The present invention relates to a pure chlorine dioxide solution, and a gel-like composition and a foaming composition each comprising the same.

BACKGROUND ART

It is well known that chlorine dioxide gas is a strong oxidant, and its oxidizing action is effective in sterilization and decomposition of malodorous substances. Therefore, chlorine dioxide has been used in disinfectant, deodorant and the like. Chlorine dioxide is dissolved in water in 20 times its volume of water, to give a brownish yellow aqueous solution. From the viewpoint of easiness in handling, it is desirable to use chlorine dioxide in a form of such an aqueous solution. However, when the aqueous solution of chlorine dioxide is brought into contact with air, chlorine dioxide gas is rapidly generated. Therefore, there has been proposed a technique in which chlorine dioxide gas is constantly generated while maintaining its stability, by dissolving chlorine dioxide gas in an aqueous solution of sodium peroxycarbonate ($Na_2C_2O_6$), and thus by forming an aqueous solution containing sodium chlorite ($NaClO_2$) as a main component at a retained pH of 9, i.e., what is called a stabilized aqueous solution of chlorine dioxide (see Patent Document 1).

However, since the stabilized aqueous solution of chlorine dioxide is retained at pH 9 (alkali) for the purpose of maintaining stability, sodium chlorite is dissociated in the aqueous solution as represented by the following equation (1):

$$NaClO_2 \rightarrow Na^+ + ClO_2^- \tag{1}$$

Therefore, a generation amount of free chlorine dioxide gas having disinfecting and deodorizing effects or the like is extremely low, and thus it is difficult to attain satisfactory disinfecting and deodorizing effects or the like.

Therefore, it has been proposed that, immediately before its use, a stimulant is added to the stabilized aqueous solution of chlorine dioxide, or an acid is added to lower the pH to 7 or less, for generating chlorine dioxide gas. However, with this technique there arise economical problems that equipments or facilities to implement the processes are required.

In addition, when a stimulant or acid is added in advance to the stabilized aqueous solution of chlorine dioxide, the concentration of the generated chlorine dioxide gas and the retention of the generation depend solely on the concentration of the stabilized aqueous solution of chlorine dioxide, and therefore there is a problem that the concentration of the generated chlorine dioxide gas and the retention of the generation cannot be controlled for the intended use. There is also a problem that chlorine dioxide gas cannot be effectively used for simple disinfection and deodorization of inside of a room, automobile, refrigelator or the like, even though it is effectively used for a large-scale deodorizing treatment of waste gas, organic waste substance and the like generated at business institutions, such as factories.

There has been also proposed a technique in which the stabilized aqueous solution of chlorine dioxide is gelatinized with a gellant, such as agar, gelatine, high water-absorbent resin and the like, to form a gel-like composition. However, with this gel-like composition, the amount of chlorine dioxide gas generation is extremely small, and there is a problem that disinfecting and deodorizing action and the like cannot be satisfactorily obtained.

In order to solve the above-mentioned problems, there has been proposed a technique in which a mixture prepared by adding an organic acid, such as citric acid, to chlorite is blended with a dissolved chlorine dioxide solution, to thereby maintain a chlorine dioxide concentration nearly constant for a long term (see Patent Document 2).

Patent Document 1: Japanese Patent Application JP61-181532A

Patent Document 2: Japanese Patent JP3110724B

DISCLOSURE OF THE INVENTION

According to the technique disclosed in Patent Document 2, the chlorine dioxide concentration can be maintained constant for a long term without rapidly generating gas, and even when chlorine dioxide is continuously released by portions as gas, the chlorine dioxide concentration can be held in an approximately constant range. However, the preservation stability is not necessarily satisfactory, and there is a room for improvement.

The present invention is made with the view toward solving the above-mentioned problems, and the object is to provide a pure chlorine dioxide solution having excellent preservation stability, in which the chlorine dioxide concentration can be held in an approximately constant range for a longer term.

In one aspect of the present invention, the pure chlorine dioxide solution includes a chlorine dioxide gas dissolved therein, a chlorite and a pH adjuster which is an acid (organic acid, inorganic acid) or a salt thereof having a buffering property whose pH is 2.5 to 6.8 as a 5% aqueous solution at 25° C. The expression "pure chlorine dioxide" herein means that chlorine dioxide is present in a form of chlorine dioxide gas, and the expression "pure chlorine dioxide solution" means a solution in which chlorine dioxide is dissolved as chlorine dioxide gas.

Herein, it is preferable that the chlorite is sodium chlorite.

In addition, it is preferable that the pH adjuster is phosphoric acid or a salt thereof.

In addition, it is preferable that the pH adjuster is sodium dihydrogenphosphate or a mixture of sodium dihydrogenphosphate with disodium hydrogenphosphate.

In another aspect of the present invention, the gel-like composition includes: a pure chlorine dioxide solution including a chlorine dioxide gas dissolved therein, a chlorite and a pH adjuster; and a high water-absorbent resin, the pH adjuster being an acid or a salt thereof having a buffering property whose pH is 2.5 to 6.8 as a 5% aqueous solution at 25° C.

Herein, it is preferable that the high water-absorbent resin is a starch-containing water-absorbent resin, a cellulose-containing water-absorbent resin or a synthetic polymer-containing water-absorbent resin.

In addition, it is preferable that the chlorite is sodium chlorite.

In addition, it is preferable that the pH adjuster is phosphoric acid or a salt thereof.

In addition, it is preferable that the pH adjuster is sodium dihydrogenphosphate or a mixture of sodium dihydrogenphosphate with disodium hydrogenphosphate.

In still another aspect of the present invention, the foaming composition includes: a pure chlorine dioxide solution including: a chlorine dioxide gas dissolved therein, a chlorite and a pH adjuster; and a foam agent, the pH adjuster being an acid or a salt thereof having a buffering property whose pH is 2.5 to 6.8 as a 5% aqueous solution at 25° C.

Herein, it is preferable that the foam agent includes a surfactant and a foam stabilizer.

In addition, it is preferable that the foam agent includes a surfactant, a foam stabilizer and an aerosol propellant.

In addition, it is preferable that the chlorite is sodium chlorite.

In addition, it is preferable that the pH adjuster is phosphoric acid or a salt thereof.

In addition, it is preferable that the pH adjuster is sodium dihydrogenphosphate or a mixture of sodium dihydrogenphosphate with disodium hydrogenphosphate.

According to the present invention, there is provided a pure chlorine dioxide solution in which chlorine dioxide can be dissolved therein at a high concentration, while the concentration being arbitrarily controlled between high and low concentrations, and chlorine dioxide gas retained at a nearly constant concentration with drug efficacy can be released for a long term. In addition, a gel-like composition and a foaming composition each containing this solution can be provided at low cost. Moreover, the pure chlorine dioxide solution, and the gel-like composition and the foaming composition each containing the same, can be simply and effectively used as antimicrobial agent or disinfectant, antiviral agent, fungicide or antifungal agent, and deodorant.

According to the present invention, excellent preservation stability can be obtained. For example, the chlorine dioxide concentration of the solution containing chlorine dioxide can be maintained constant for a long term, and even when chlorine dioxide is continuously released by portions as gas from the solution (or even when chlorine dioxide gas is aggressively kept released), the chlorine dioxide concentration in the solution can be held in an approximately constant range. The expression "continuously released by portions as gas" herein means that, for example, during transportation or preservation, even though a lid of a container is closed, chlorine dioxide dissipates as gas in the course of nature, and the expression "chlorine dioxide gas is aggressively kept released" herein means that chlorine dioxide gas is released to a gas phase with an expectation of obtaining deodorizing and disinfecting action in the gas phase.

When phosphoric acid or a salt thereof is used as the pH adjuster, as compared with other inorganic acids or organic acids, preservation stability is further improved (period with preservation stability is further extended), and a change in a liquid property (pH) over time during preservation is suppressed. Especially, it is preferable to use sodium dihydrogenphosphate or a mixture of sodium dihydrogenphosphate with disodium hydrogenphosphate, from the viewpoint of preservation stability.

Moreover, by selecting sodium dihydrogenphosphate or the mixture of sodium dihydrogenphosphate with disodium hydrogenphosphate, and by combining this with sodium chlorite, an excessive progression of a reaction in which sodium chlorite turns into chlorine dioxide hardly occurs. Therefore, a gas equilibration state is retained by replenishing chlorite ion from sodium chlorite that compensates only chlorine dioxide that is lost by natural decomposition or that dissipates from a lid portion or walls of the container. As described above, the present invention is suitable in that unnecessary consumption of sodium chlorite is suppressed and sodium chlorite is efficiently consumed, leading to further improvement in preservation stability (period with preservation stability is further extended), and to further suppression of a change in the chlorine dioxide concentration over time during preservation (both the decrease and increase in the concentration can be suppressed). In addition, a mechanism of the solution for replenishing chlorine dioxide from sodium chlorite for a long term is exerted even in a space or on a subject, to which the solution is applied, sprayed or diffused. This provides an excellent sustained effect, i.e. lasting disinfecting and deodorizing activity after application, spraying or diffusion of the solution, further providing a great merit to the user upon its use.

BEST MODE FOR CARRYING OUT THE INVENTION

Figure 1:
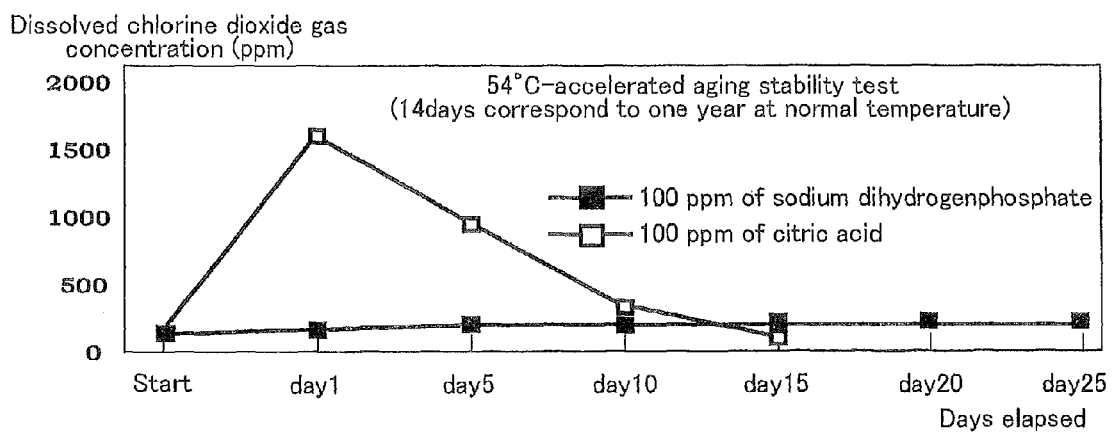
FIG. 1 is a graph showing dissolved chlorine dioxide gas concentration in a case where sodium dihydrogenphosphate was used in an amount of a reaction equivalent or more and a case where citric acid was used in an amount of a reaction equivalent or more (the initial concentration was 100 ppm)
Figure 2:
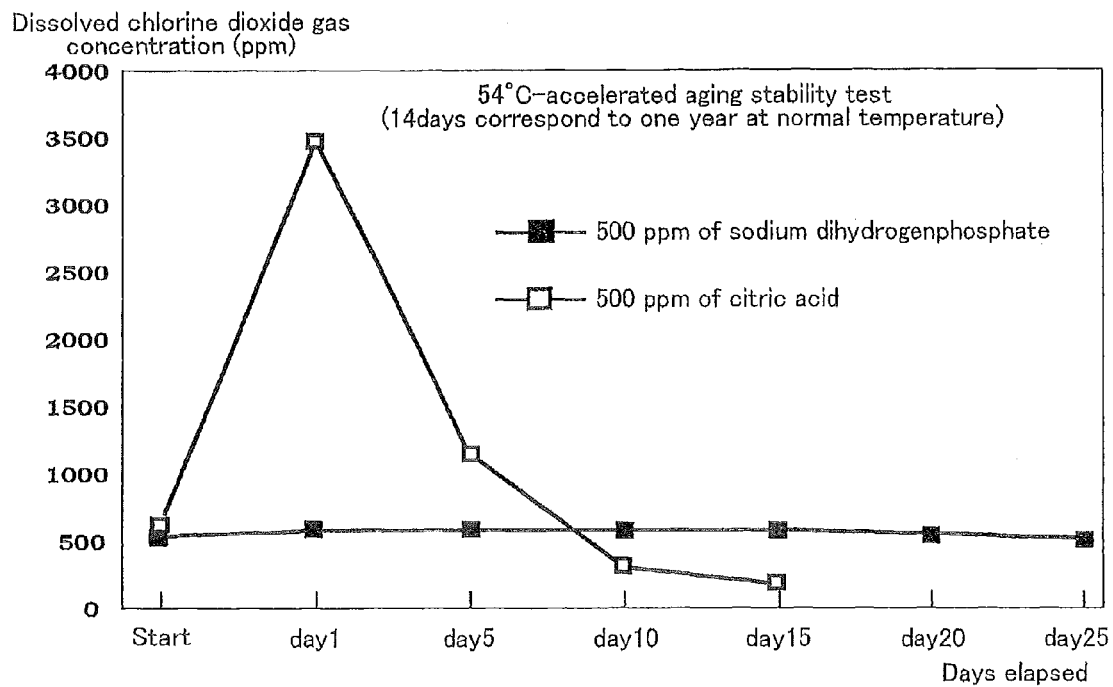
FIG. 2 is a graph showing dissolved chlorine dioxide gas concentration in a case where sodium dihydrogenphosphate was used in an amount of a reaction equivalent or more and a case where citric acid was used in an amount of a reaction equivalent or more (the initial concentration was 500 ppm).

An embodiment of the present invention will be described below, but the present invention should not be limited to this embodiment.

(Chlorite)

For the chlorite to be used in the present invention, for example, salts of alkali metal chlorite and salts of alkali earth metal chlorite can be mentioned. Examples of the salt of alkali metal chlorite include sodium chlorite, potassium chlorite and lithium chlorite. Examples of the salt of alkali earth metal chlorite include calcium chlorite, magnesium chlorite and barium chlorite. Especially, not only from the viewpoint of availability, but also from the viewpoint of sustention of chlorine dioxide gas generation, sodium chlorite and potassium chlorite are preferable, and sodium chlorite is more preferable.

(pH Adjuster)

For the pH adjuster to be used in the present invention, an acid (inorganic acid and organic acid) or a salt thereof having a buffering property whose pH is 2.5 to 6.8 as a 5% aqueous solution at 25° C., can be mentioned. When the pH is below 2.5, or above 6.8, the preservation stability of the dissolved chlorine dioxide is reduced, and a change in a liquid property (pH) of the chlorine dioxide solution during preservation becomes large. It is preferable to use an acid (inorganic acid and organic acid) or a salt thereof having a buffering property whose pH is 3.5 to 6.0 as a 5% aqueous solution at 25° C., and it is more preferable to use one whose pH is 4.0 to 5.5. Examples of the acid include phosphoric acid, boric acid, metaphosphoric acid, pyrophosphoric acid, sulfamic acid and acetic acid, and from the viewpoint of obtaining excellent preservation stability, inorganic acid or a salt thereof is preferred. Examples of the salt thereof include sodium dihydrogenphosphate and a mixture of sodium dihydrogenphosphate with disodium hydrogenphosphate. Especially, phosphoric acid or a salt thereof is preferred, and sodium dihydrogenphosphate is more preferred, since preservation stability is excellent and a change in the liquid property (pH) during preservation is suppressed to a minimum, leading to excellent disinfecting action, antiviral action, antifungal action, deodorizing action or the like. It should be noted that one kind of the pH adjuster may be used alone or two or more kinds thereof may be used in combination. The final pure chlorine dioxide solution has a pH of preferably 4.5 to 6.5, more preferably 5.5 to 6.0, since preservation stability is excellent for a long term, and a pH change during preservation is suppressed.

(High Water-Absorbent Resin)

The pure chlorine dioxide solution of the present invention including the chlorine dioxide gas dissolved therein, the chlorite and the pH adjuster (an acid or a salt thereof having a buffering property whose pH is 2.5 to 6.8 (preferably 3.5 to 6.0, more preferably 4.0 to 5.5) as a 5% aqueous solution at 25° C.) may be mixed with a high water-absorbent resin and prepared as a gel-like composition. Examples of the high water-absorbent resin include a starch-containing water-absorbent resin (e.g., grafted starch-containing high water-absorbent resin, such as starch-acrylonitrile graft copolymer, starch-acrylic acid graft copolymer, starch-styrenesulfonic acid graft copolymer and starch-vinylsulfonic acid graft copolymer), a cellulose-containing water-absorbent resin (e.g., cellulose-containing high water-absorbent resin, such as cellulose-acrylonitrile graft copolymer, cellulose-styrenesulfonic acid graft copolymer, and cross-linked carboxymethyl cellulose; phosphoric-esterified paper and cloth; and carboxymethylated cloth), and a synthetic polymer-containing water-absorbent resin (e.g. polyvinyl alcohol-containing high water-absorbent resin, such as cross-linked polyvinyl alcohol; acrylic high water-absorbent resin, such as cross-linked polyacrylate, saponified polyacrylonitrile-containing polymer and cross-linked polyethylene glycol dimethacrylate; and cross-linked polyethylene oxide-containing high water-absorbent resin).

Examples of those commercially available include a starch/polyacrylic acid resin [Sanwet (powder, manufactured by Sanyo Chemical Industries Ltd.)], a cross-linked polyacrylic acid resin [Aqualic (powder, manufactured by Nippon Shokubai, Co., Ltd.), Arasorb (powder, manufactured by Arakawa Chemical Industries, Ltd.), Wondergel (powder, manufactured by Kao Corporation), Aqua Keep (powder, manufactured by Sumitomo Seika Chemicals, Co., Ltd.), Diawet (powder, manufactured by Mitsubishi Petrochemical Co., Ltd.)], an isobutylene/maleic acid resin [KI gel (powder, manufactured by Kuraray Co., Ltd.)], and a poval/polyacrylic acid salt resin [Sumikagel (powder, manufactured by Sumitomo Chemical Co., Ltd.)]. Use of these will not hinder the present invention.

(Foam Agent)

Further, the pure chlorine dioxide solution of the present invention including the chlorine dioxide gas dissolved therein, the chlorite and the pH adjuster (an acid or a salt thereof having a buffering property whose pH is 2.5 to 6.8 (preferably 3.5 to 6.0, more preferably 4.0 to 5.5) as a 5% aqueous solution at 25° C.) may be mixed with a foam agent and prepared as a foaming composition.

The foam agent may be formed of (1) a surfactant and a foam stabilizer, or (2) a surfactant, a foam stabilizer and an aerosol propellant.

Examples of the surfactant include, but are not restricted to, (1) at least one anionic surfactant selected from: a carboxylate salt, such as polyoxyethylene alkyl ether carboxylate; a sulfonate salt, such as alkylbenzenesulfonate and alkylnaphthalenesulfonate; a salt of sulfuric acid ester, such as salt of sulfuric acid higher alcohol ester; and a salt of phosphoric acid ester, such as polyoxyethylene alkyl ether phosphate, (2) a cationic surfactant, such as fatty acid quaternary ammonium salt, (3) a carboxybetaine type ampholytic surfactant, (4) a nonionic surfactant, such as polyoxyethylene alkyl ether, polyoxyethylene glycerin fatty acid ester, polyethylene glycol fatty acid ester, and fatty acid alkanolamide, (5) a fluorine-containing surfactant, and (6) a saponin.

Examples of the foam stabilizer include, but are not restricted to, (7) a stabilizer prepared by adding mono- or di-ethanolamine to the above-mentioned anionic surfactant, (8) a stabilizer prepared by adding a long-chain alcohol or alkylsulfoxide to the above-mentioned nonionic surfactant, and (9) liquid paraffin.

Examples of the aerosol propellant include, but are not restricted to, a high-pressure gas with low toxicity, such as liquefied natural gas (LPG), liquefied butane and dimethyl ether.

(Preparative Example of Chlorine Dioxide Solution)

The pure chlorine dioxide solution of the present invention may be, for example, obtained in the following manner. Specifically, (a) a chlorite is dissolved in water to prepare 2,000 to 180,000 ppm of an aqueous chlorite solution, (b) chlorine dioxide gas is bubbled and dissolved in water to prepare 100 to 2,900 ppm of an aqueous solution of chlorine dioxide, and (c) a chlorite is dissolved in water to prepare 2,000 to 180,000 ppm of an aqueous chlorite solution, and in the solution is dissolved a pH adjuster (an acid or a salt thereof having a buffering property whose pH is 2.5 to 6.8 as a 5% aqueous solution at 25° C.) in an amount of 0.5 to 100 g per 1,000 ml of the solution, to prepare an aqueous chlorite solution containing the pH adjuster.

Subsequently, 5.0 to 990 ml, preferably 50 to 300 ml of the aqueous solution of chlorous acid (item (a)), 5.0 to 990 ml, preferably 50 to 800 ml of the aqueous solution of chlorine dioxide (item (b)) and 5.0 to 990 ml, preferably 50 to 400 ml of the aqueous solution of chlorous acid containing the pH adjuster (item (c)) are mixed and stirred well at room temperature to thereby prepare a pure chlorine dioxide solution.

It is preferred that the final pH of the pure chlorine dioxide solution is 4.5 to 6.5. When the pH is out of this range, the preservation stability is reduced, which may lead to, for example, fluctuation of the pharmacological activity during preservation, and to attenuation in the pharmacological activity after long-term (e.g. 2-year) preservation. In the present invention, more preferable pH range of the pure chlorine dioxide solution is 5.5 to 6.0.

(Gel-Like Composition)

In the case where the gel-like composition is obtained by admixing with the high water-absorbent resin, for example, 50 to 99 weight % of the pure chlorine dioxide solution prepared in the above-described manner is added to 1.0 to 50 weight % of the high absorbent resin (powder), and stirred well at room temperature. Such a "gel-like composition" may be, for example, of general utility as being filled in a container having an opening on at least one side (see Japanese Patent Application JP61-40803A), or alternatively, of general utility as being filled in a container formed of paper or nonwoven fabric containing synthetic fiber as constituent fiber, with rims thereof sealed by heat-sealing the synthetic fiber or by a synthetic-resin adhesive. Examples of the synthetic fiber include the conventional thermoplastic synthetic fiber, such as polypropylene fiber, polyester fiber and polyamide fiber. In the case of the container formed of paper or nonwoven fabric containing such synthetic fiber as constituent fiber, it is possible to prevent clogging of the container which may otherwise be caused by the attached "gel-like composition", and at the same time to sustainably evaporate chlorine dioxide from the "gel-like composition".

(Foaming Composition)

In the case where the foaming composition is prepared by adding the foam agent, the foaming composition may be prepared, for example, in a closed container, by adding 5.0 to 20 weight % of the foam stabilizer and 60 to 95 weight % of the surfactant to 1.0 to 20 weight % of the pure chlorine dioxide solution as prepared above and stirring the mixture well at room temperature. Such a "foaming composition" may be of general utility as enclosed in, for example, a trigger type foaming container, a pump type foaming container or the like, conventionally used for cosmetic product, detergent, fungicide or the like.

(Other Usage and Applications)

Since the main component is the dissolved chlorine dioxide gas, the "pure chlorine dioxide solution" of the present invention has excellent safety to humans, animals and the like, and for example, a disinfection (hereinafter, the term "disinfection" also includes viral inactivation) and deodorizing treatment can be performed on drinkable water, food processing water, pool water or the like, by adding the solution thereto. In addition, vegetables, table wares, kitchen linens or the like can be disinfected by immersing them into an aqueous solution prepared by diluting the solution nearly 10-fold with water. Moreover, kitchen facilities at hotels, restaurants, catering industry, schools and household, rooms of house, lavatory pans, car interiors or the like can be disinfected and deodorized, by spraying a dilution onto them prepared by diluting the solution nearly 5-fold.

The "pure chlorine dioxide solution" of the present invention may also be mixed with highly superabsorbent resin, and the resultant gel-like composition can be used for an antimicrobial and deodorizing treatment of inside of a refrigerator, bathroom, room, automobile or the like.

In addition, the "pure chlorine dioxide solution" of the present invention is mixed with a foam agent as a foaming composition, and effectively utilized for an antimicrobial and deodorizing treatment of, for example, diapers used in nursing care, a grease trap installed in a restaurant kitchen, a place for food scrap and industrial waste (e.g. sludge), and for fungicidal treatment of tiles, walls and the like. The foam agent may be formed of (1) a surfactant and a foam stabilizer, or (2) a surfactant, a foam stabilizer and an aerosol propellant. The production cost will be higher in the latter, but a large amount of foam can be obtained with a small amount of the agent (because of air intake), and thus effectively used for high-value added and smaller objects, such as diapers used in nursing care, and a grease trap installed in a restaurant kitchen. Since the foaming composition of the present invention as form can widely cover an object on which an antimicrobial and deodorizing treatment is to be performed, and the foam is present in a state of layer, an antimicrobial and deodorizing treatment can be reliably performed and sustension of an antimicrobial and deodorizing activity can be enhanced.

In this manner, the pure chlorine dioxide solution, and the gel-like composition and the foaming composition each including the same of the present invention can simply and effectively used for various applications.

Example 1

In the following manner, a chlorine dioxide solution was prepared. Specifically, to 250 ml of water in which 2,000 ppm of chlorine dioxide gas had been dissolved were added 680 ml of water and then 80 ml of a 25% solution of sodium chlorite, and stirred. Subsequently, to the solution was added sodium dihydrogenphosphate (having a pH of 4.1 to 4.5 as a 5% aqueous solution at 25° C.) in such an amount that the pH of the solution became 5.5 to 6.0 and stirred, to thereby obtain 1,000 ml of a chlorine dioxide solution including a chlorine dioxide gas dissolved therein, sodium chlorite, and sodium dihydrogenphosphate.

Comparative Example 1

A chlorine dioxide solution as a control was prepared in the same manner as in Example 1, except that citric acid (having a pH of 1.8 to 2.2 as a 5% aqueous solution at 25° C.) was used instead of sodium dihydrogenphosphate.

Example 2

To 16 g of cross-linked polyacrylate-containing high water-absorbent resin [Aqualic (powder, manufactured by Nippon Shokubai, Co., Ltd.)] was added 384 ml of the chlorine dioxide solution prepared in the same manner as in Example 1, and the mixture was stirred well at room temperature to thereby obtain 400 g of a light yellow gel-like composition.

Example 3

To a closed container were added 160 ml of the chlorine dioxide solution prepared in the same manner as in Example 1, 30 ml of a surfactant formed of sodium alkylsulfonate, 10 g of liquid paraffin, and 100 g of aerosol propellant formed of liquefied butane, and the mixture was stirred well at room temperature to thereby obtain 300 g of a light yellow foaming composition.

Next, the action of the present invention will be described. In the case where chlorine dioxide gas is dissolved in water, an equilibrium reaction and an equilibrium constant are represented by, for example, the following equations (2) and (3), respectively.

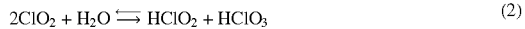

$$2ClO_2 + H_2O \rightleftharpoons HClO_2 + HClO_3 \qquad (2)$$

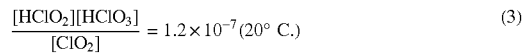

$$\frac{[HClO_2][HClO_3]}{[ClO_2]} = 1.2 \times 10^{-7} (20°\ C.) \qquad (3)$$

As shown by the equations (2) and (3), chlorine dioxide gas ($ClO_2$) is predominantly present in a form of dissolved chlorine dioxide at normal temperature.

When sodium chlorite and sodium dihydrogenphosphate, respectively as chlorite and pH adjuster (an acid or a salt thereof having a buffering property whose pH is 2.5 to 6.8 as a 5% aqueous solution at 25° C.), are added to the aqueous solution of chlorine dioxide dissolved therein, the pH of the solution can be retained acidic, and at the same time, a rapid change of a pH can be suppressed. Due to the presence of sodium dihydrogenphosphate, sodium chlorite is ionized in water to generate chlorous acid, as represented by the following equation (4):

$$NaClO_2 + H^+ \rightarrow Na^+ + HClO_2 \qquad (4)$$

When chlorous acid is generated in this manner, the reaction advances to the left in the equation (2) in an equilibrium state, in other words, a reverse reaction progresses. Therefore, in the case where sodium chlorite and sodium dihydrogenphosphate are present in an aqueous solution of chlorine dioxide gas, when the concentration of the dissolved chlorine dioxide is below the maximum (2,900 ppm), the concentration of the dissolved chlorine dioxide gas is increased. For this reason, the "pure chlorine dioxide solution" of the present invention can contain a high concentration of chlorine dioxide dissolved therein.

In addition, among four different compounds in the equation (2), $ClO_2$ is most reactive and likely to be volatilized from the aqueous solution (boiling point of 11° C., vapor pressure of 500 torr (0° C.)), and the reaction advances to the left in the equation (2), in other words, a reverse reaction progresses. Therefore, a decrease in the dissolved chlorine dioxide is always replenished with chlorous acid derived from sodium chlorite.

Moreover, sodium dihydrogenphosphate not only makes the pH of the pure chlorine dioxide solution of the present invention acidic, but it also functions as a buffer that suppresses a rapid change in a pH. As a result, in the equation (4), a rapid change from sodium chlorite to chlorous acid is suppressed, and in the equation (2), a rapid increase in the release of the dissolved chlorine dioxide is suppressed, which in turn suppresses the lowering of sustention of action, such as antimicrobial and deodorizing action, of the solution.

Therefore, according to the "pure chlorine dioxide solution" of the present invention, chlorine dioxide can be dissolved therein at a high concentration, while the concentration being arbitrarily controlled between high and low concentrations, and chlorine dioxide gas retained at a nearly constant concentration with drug efficacy can be released for a long term, by replenishing the dissolved chlorine dioxide which was released. Moreover, a rapid increase in the release of the dissolved chlorine dioxide is suppressed, which in turn suppresses the lowering of sustention of action, such as antimicrobial and deodorizing action, of the solution. Such excellent action of the "pure chlorine dioxide solution" of the present invention is also exerted in the "gel-like composition" and the "foaming composition" of the present invention.

Since the "pure chlorine dioxide solution" of the present invention includes the chlorine dioxide gas dissolved therein as a main component, it can be extremely effectively used, for example, for an antimicrobial treatment or disinfection of *Escherichia coli* (O-157), *salmonella*, *Staphylococcus aureus* and *Clostridium botulinum*; antiviral treatment against viruses, such as influenza virus, avian influenza virus, norovirus (feline calicivirus), human papilloma virus, coxsackievirus, AIDS virus, hepatitis B virus, canine parvovirus, rotavirus, HHV-1 (herpes simplex virus type 1 (HSV-1)), HHV-2 (herpes simplex virus type 2 (HSV-2)), HHV-3 (varicella-zoster virus (VZV)), and HHV-5 (cytomegalovirus (CMV)); antifungal or fungicidal treatment against various fungi; and deodorizing treatment for cigarette smell, body odor and various smells of food products.

As described above, the conventional "stabilized chlorine dioxide" is an aqueous solution containing sodium chlorite ($NaClO_2$) as a main component and is retained at a pH of 9 (alkali), and $NaClO_2$ is dissociated as represented by the equation (1). Since $ClO_2^-$ in an aqueous solution forms a hydrogen bonding with a water molecule, only a trace amount of free chlorine dioxide gas ($ClO_2$) volatilizes and its oxidixing power is very weak. It should be noted that the expression "stabilized chlorine dioxide" herein means chlorine dioxide in which chlorine dioxide gas is altered and present in a form of sodium chlorite. On the other hand, an oxidizing power of the "pure chlorine dioxide solution" of the present invention is very strong, since it is derived from $ClO_2$ dissolved in water. Therefore, an antimicrobial capability of the "pure chlorine dioxide solution" of the present invention is 360 times as effective as that of the conventional "stabilized chlorine dioxide". In addition, an antimicrobial concentration of the "pure chlorine dioxide solution" of the present invention is 0.1 ppm or more, while an antimicrobial concentration of the conventional "stabilized chlorine dioxide" is 300 ppm or more. Furthermore, contact rate of the "pure chlorine dioxide solution" of the present invention of chlorine dioxide gas with microbes is overwhelmingly high as compared with the conventional "stabilized chlorine dioxide".

As described above, there has been proposed a technique in which, immediately before its use, a stimulant is adequately added to the aqueous solution of the conventional "stabilized chlorine dioxide", or an acid is added to lower the pH to 7 or less, for temporally increasing the concentration of the chlorine dioxide. On the other hand, in the case of the "pure chlorine dioxide solution" of the present invention, without adding such a stimulant or acid, chlorine dioxide can be dissolved therein at a high concentration, while the concentration being arbitrarily controlled between high and low concentrations, and chlorine dioxide gas retained at a nearly constant concentration with drug efficacy can be released for a long term. Therefore, high drug efficacy can be continuously retained for a long term. In addition, the present invention exhibits more excellent preservation stability of the pure chlorine dioxide solution, and high drug efficacy can be retained for a longer term, as compared with the previously proposed technique (disclosed in Japanese patent No. 3110724). The pure chlorine dioxide solution of the present invention, the gel-like composition and the foaming composition each containing the same can be simply and effectively applied as antimicrobial agent or disinfectant, antiviral agent, fungicide or antifungal agent, and deodorant.

(Stabilizing Test)

The chlorine dioxide solution obtained in Example 1 was diluted by a conventional method, to thereby prepare chlorine dioxide solutions having concentrations of 100 ppm and 500 ppm. Likewise, the chlorine dioxide solution obtained in Comparative Example 1 was used to thereby prepare solutions having chlorine dioxide concentrations of 100 ppm and 500 ppm.

In order to determine the preservation stability of these solutions, a change in the dissolved chlorine dioxide concentration (ppm) over time was measured. For the stabilizing test, an accelerated aging test (measurement temperature: 54° C., 14 days correspond to one year at normal temperature) was performed in accordance with a conventional method. The results of the preservation stability are shown in Tables below and the drawings (comparative data is shown between a case where sodium dihydrogenphosphate was used in an amount of a reaction equivalent or more and a case where citric acid was used in an amount of a reaction equivalent or more).

TABLE 1

*54° C.-accelerated aging test (14 days correspond to one year at normal temperature)

Dissolved $ClO_2$ (ppm)

(Concentration: 100 ppm, sodium dihydrogenphosphate was used)

| | |
|---|---|
| Start | 116 |
| 1 day later | 143 |
| 5 days later | 154 |
| 10 days later | 149 |
| 15 days later | 128 |
| 20 days later | 128 |
| 25 days later | 129 |

TABLE 1-continued

*54° C.-accelerated aging test (14 days correspond to one year at normal temperature)

Dissolved ClO$_2$ (ppm)

(Concentration: 100 ppm, citric acid was used)

| | |
|---|---|
| Start | 121 |
| 1 day later | 1,551 |
| 5 days later | 935 |
| 10 days later | 269 |
| 15 days later | 69 |
| 20 days later | — |
| 25 days later | — |

TABLE 2

*54° C.-accelerated aging test (14 days correspond to one year at normal temperature)

Dissolved ClO$_2$ (ppm)

(Concentration: 500 ppm, sodium dihydrogenphosphate was used)

| | |
|---|---|
| Start | 523 |
| 1 day later | 554 |
| 5 days later | 546 |
| 10 days later | 532 |
| 15 days later | 538 |
| 20 days later | 516 |
| 25 days later | 476 |

(Concentration: 500 ppm, citric acid was used)

| | |
|---|---|
| Start | 567 |
| 1 day later | 3,474 |
| 5 days later | 1,160 |
| 10 days later | 286 |
| 15 days later | 150 |
| 20 days later | — |
| 25 days later | — |

As is apparent from the above-described tables and accompanied drawings, the pH adjuster whose pH is 2.5 to 6.8 as a 5% aqueous solution at 25° C. remarkably enhances the preservation stability of the chlorine dioxide solution, and suppresses a change in the liquid property (pH) during preservation, as compared with an acid having a buffering property whose pH is outside the range of from 2.5 to 6.8.

INDUSTRIAL APPLICABILITY

The present invention is suitably used as, for example, antimicrobial agent or disinfectant, antiviral agent, fungicidal agent or fungicide, and deodorant.

The invention claimed is:

1. A gel-like composition, comprising a pure chlorine dioxide solution and a high water-absorbent resin,
   wherein said pure chlorine dioxide solution is prepared by the following steps:
   [1] mixing a solution (A) which is a solution in which a chlorine dioxide gas is dissolved, and a solution (B) which is a solution comprising a chlorite; and
   [2] adding a pH adjuster to the solution mixture resulting from step [1], wherein the pH adjuster is phosphoric acid or a salt thereof having a buffering property whose pH is 2.5 to 6.8 as a 5% aqueous solution at 25° C.,
   wherein said pure chlorine dioxide solution is stable for at least 15 days according to a 54° C.-accelerated aging stability test.

2. The gel-like composition according to claim 1, wherein the high water-absorbent resin is one of a starch-containing water-absorbent resin, a cellulose-containing water-absorbent resin and a synthetic polymer-containing water-absorbent resin.

3. The gel-like composition according to claim 1, wherein the chlorite is sodium chlorite.

4. The gel-like composition according to claim 1, wherein the pH adjuster is one of sodium dihydrogenphosphate and a mixture of sodium dihydrogenphosphate with disodium hydrogenphosphate.

5. The gel-like composition according to claim 1, wherein the high water-absorbent resin is one of a starch-containing water-absorbent resin, a cellulose-containing water-absorbent resin and a synthetic polymer-containing water-absorbent resin, wherein the chlorite is sodium chlorite, and wherein the pH adjuster is one of sodium dihydrogenphosphate and a mixture of sodium dihydrogenphosphate with disodium hydrogenphosphate.

* * * * *